(12) United States Patent
Wang

(10) Patent No.: US 7,426,025 B2
(45) Date of Patent: Sep. 16, 2008

(54) NANOSTRUCTURES, SYSTEMS, AND METHODS INCLUDING NANOLASERS FOR ENHANCED RAMAN SPECTROSCOPY

(75) Inventor: Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 315 days.

(21) Appl. No.: 11/233,686

(22) Filed: Sep. 23, 2005

(65) Prior Publication Data
US 2007/0070341 A1   Mar. 29, 2007

(51) Int. Cl.
*G01J 3/44* (2006.01)
(52) U.S. Cl. ........................... 356/301; 977/951
(58) Field of Classification Search ............... 356/301; 977/951
See application file for complete search history.

(56) References Cited

U.S. PATENT DOCUMENTS

| | | | |
|---|---|---|---|
| 4,245,370 A * | 1/1981 | Baker | 15/319 |
| 6,882,051 B2 | 4/2005 | Majumdar et al. | |
| 7,102,747 B2 * | 9/2006 | Wang et al. | 356/301 |
| 7,158,219 B2 * | 1/2007 | Li et al. | 356/36 |
| 2002/0129761 A1 | 9/2002 | Takami | |
| 2002/0172820 A1 | 11/2002 | Majumdar et al. | |
| 2003/0030067 A1 | 2/2003 | Chen | |
| 2003/0135971 A1 | 7/2003 | Liberman et al. | |
| 2003/0213428 A1 | 11/2003 | Lu et al. | |
| 2004/0213307 A1 | 10/2004 | Lieber et al. | |
| 2004/0244677 A1 | 12/2004 | Takami | |
| 2006/0240588 A1 * | 10/2006 | Conley et al. | 438/49 |

OTHER PUBLICATIONS

Duan, Xiangfeng, et al., Single-nanowire electrically driven lasers, Nature, vol. 421, pp. 241-245, Jan. 16, 2003.
Huang, Michael H., et al., Room-Temperature Ultraviolet Nanowire Nanolasers, Science, vol. 292, pp. 1897-1899, Jun. 8, 2001.
Huang, Michael H., et al., Catalytic Growth of Zinc Oxide Nanowires by Vapor Transport, Adv. Mater., vol. 13, No. 2, pp. 113-116, Jan. 16, 2001.
Johnson, Justin C., et al., Single gallium nitride nanowire lasers, Nature Materials, vol. 1, pp. 106-110, Oct. 2002.

* cited by examiner

*Primary Examiner*—L. G Lauchman

(57) ABSTRACT

Nanostructures configured to enhance the intensity of Raman scattered radiation scattered by an analyte include a substantially planar substrate, a plurality of nanoparticles disposed on a surface of the substrate, and a Raman-enhancing material disposed on at least a portion of at least one nanoparticle. Each nanoparticle is configured to emit lased radiation upon stimulation of the nanoparticle and may comprise a nanowire laser. Raman spectroscopy systems include a radiation source, a radiation detector configured to detect Raman scattered radiation scattered by an analyte, a nanostructure including at least one nanoparticle configured to emit lased radiation upon stimulation, and means for stimulating the nanoparticle. Methods for performing Raman spectroscopy include providing a nanostructure including at least one nanoparticle configured to emit lased radiation upon stimulation of the nanoparticle, providing an analyte proximate to the nanoparticle, stimulating the nanoparticle, and detecting Raman scattered radiation.

21 Claims, 4 Drawing Sheets

▼ = Antigen
𝖸𝖿 = Antibody

NANOSTRUCTURES, SYSTEMS, AND METHODS INCLUDING NANOLASERS FOR ENHANCED RAMAN SPECTROSCOPY

FIELD OF THE INVENTION

The present invention relates to Raman spectroscopy. More particularly, the invention relates to nanostructures configured to enhance the intensity of Raman scattered radiation that is scattered by an analyte, Raman spectroscopy systems including such nanostructures, and methods for performing Raman spectroscopy using such nanostructures.

BACKGROUND OF THE INVENTION

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. In Raman spectroscopy, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte. These inelastically scattered photons have a different wavelength than the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes, including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that allows for enhancement of the intensity of the Raman scattered radiation relative to conventional Raman spectroscopy. In SERS, the analyte molecules typically are adsorbed onto or placed adjacent to what is often referred to as a SERS-active structure. SERS-active structures typically include a metal surface or structure. Interactions between the analyte and the metal surface may cause an increase in the intensity of the Raman scattered radiation. The mechanism by which the intensity of the Raman scattered radiation is enhanced is not completely understood. Two main theories of enhancement mechanisms have been presented in the literature: electromagnetic enhancement and chemical enhancement.

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates, such as a roughened metal surface or metal "islands" formed on a substrate. For example, it has been shown that adsorbing analyte molecules onto or near a specially roughened metal surface made from gold or silver can enhance the Raman scattering intensity by factors of between $10^3$ and $10^6$.

Recently, Raman spectroscopy has been performed employing randomly oriented nanostructures, such as nanometer scale needles, particles, and wires, as opposed to a simple roughened metallic surface. This process will be referred to herein as nanostructure-enhanced Raman spectroscopy (NERS). The intensity of the Raman scattered photons from a molecule adsorbed on such a nanostructure can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science.

Hyper-Raman spectroscopy is another Raman spectroscopy technique that involves detecting higher order harmonic wavelengths of Raman scattered radiation. The hyper-Raman scattered radiation is Raman-shifted relative to integer multiples of the wavelength of the incident electromagnetic radiation. Hyper-Raman scattered radiation may provide information about the analyte that cannot be obtained from simple Raman spectroscopy. The intensity of the hyper-Raman scattered radiation, however, is even less than the intensity of the Raman scattered radiation. As a result, hyper-Raman spectroscopy may be performed using SERS-active or NERS-active structures to enhance the intensity of the hyper-Raman scattered radiation. It is understood that the term "Raman" is meant to also include hyper-Raman events.

BRIEF SUMMARY OF THE INVENTION

In one aspect, the present invention includes a nanostructure configured to enhance the intensity of Raman scattered radiation that is scattered by an analyte. The nanostructure includes a substantially planar substrate, a plurality of nanoparticles disposed on a surface of the substantially planar substrate, and a Raman-enhancing material disposed on at least a portion of at least one nanoparticle. Each nanoparticle of the plurality of nanoparticles is configured to emit lased radiation upon stimulation of the nanoparticle.

In another aspect, the present invention includes a Raman spectroscopy system. The Raman spectroscopy system includes a radiation detector configured to detect Raman scattered radiation that is scattered by an analyte and a nanostructure configured to enhance the intensity of the Raman scattered radiation. The nanostructure includes at least one nanoparticle that is configured to emit lased radiation upon stimulation of the at least one nanoparticle. The Raman spectroscopy system further includes means for stimulating the nanoparticle.

In yet another aspect, the present invention includes a method for performing Raman spectroscopy. The method includes providing a nanostructure that is configured to enhance Raman scattered radiation that is scattered by an analyte. The nanostructure includes at least one nanoparticle that is configured to emit lased radiation upon stimulation of the nanoparticle. The method further includes providing an analyte at a position proximate to the at least one nanoparticle, stimulating the at least one nanoparticle, and detecting Raman scattered radiation that is scattered by the analyte.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The term "nanostructure" as used herein means a structure that includes at least one nanoparticle.

The term "nanoparticle" as used herein means a particle of any shape having cross-sectional dimensions of less than about 100 nanometers. Examples of nanoparticles include, but are not limited to, nanodots (including quantum dots), nanowires, nanocolumns, and nanospheres.

The term "analyte" as used herein means any molecule, molecules, material, substance, or matter that is to be analyzed by Raman spectroscopy.

The term "Raman-enhancing material" as used herein means a material that, when formed into appropriate geometries or configurations, is capable of increasing the number of Raman scattered photons that are scattered by an analyte when the analyte is located proximate to that material and the analyte and material are subjected to electromagnetic radiation. Raman-enhancing materials include, but are not limited to, silver, gold, and copper.

The term "lased radiation" as used herein means coherent electromagnetic radiation that has been generated by stimulated emission.

The illustrations presented herein are not meant to be actual views of any particular nanostructure or Raman spectroscopy system, but are merely idealized representations which are employed to describe the present invention. Additionally, elements common between figures may retain the same numerical designation.

Figure 1:
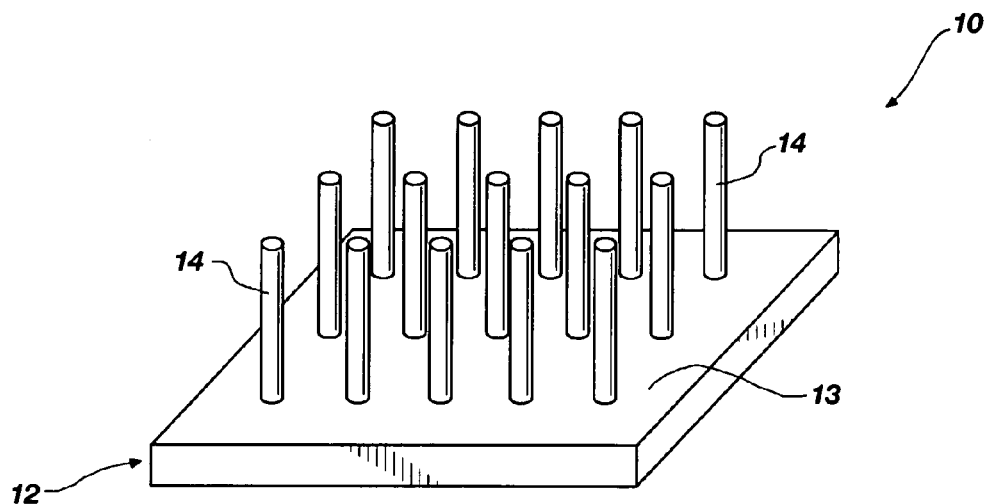
FIG. 1 is a perspective view of a representative nanostructure that embodies teachings of the present invention.

A representative nanostructure 10 that embodies teachings of the present invention is shown in FIG. 1. The nanostructure 10 may include a substantially planar substrate 12 and a plurality of nanoparticles 14. The nanoparticles 14 are disposed on a surface 13 of the substantially planar substrate 12. Each nanoparticle 14 of the plurality of nanoparticles 14 is configured to emit lased radiation upon stimulation of the nanoparticle 14.

The nanoparticles 14 may comprise nanowire lasers that extend from the surface 13 of the substantially planar substrate 12. Each nanowire laser may be elongated and may extend in a direction substantially parallel to the other nanowire lasers.

As an example, the substantially planar substrate 12 may comprise sapphire and each nanoparticle 14 may comprise a ZnO crystal. To produce such a nanostructure 10, a substantially planar substrate 12 may be provided. The surface 13 of the substantially planar substrate 12 may be oriented parallel to the (110) plane of the sapphire crystal structure. Such sapphire substrates are commercially available. A thin layer of catalyst material may be deposited and patterned on the surface 13 of the substantially planar substrate 12. The catalyst material may comprise, for example, gold. After the thin layer of catalyst material has been patterned to provide discrete regions of catalyst material having nanoscale dimensions, the ZnO nanoparticles 14 may be synthesized on the surface 13 using a vapor phase transport process employing a vapor-liquid-solid (VLS) mechanism. The ZnO nanoparticles 14 will only grow at each discrete region of catalyst material. Each ZnO nanoparticle 14 can be grown or synthesized at a predetermined location if the thin layer of catalyst material is selectively patterned to provide discrete regions of catalyst material at predetermined locations. Such patterning techniques include, for example, ion beam lithography and nanoimprinting.

Zn vapor may be generated using carbothermal or hydrogen reduction of ZnO. The ZnO nanoparticles 14 may be gown on the catalyst-coated substantially planar substrate 12 by heating a 1:1 mixture of ZnO and graphite powder to between about 900° C. and about 925° C. under a constant flow of argon for between about 5 minutes and about 30 minutes. The resulting ZnO nanoparticles 14 may have a diameter of less than about 150 nanometers and lengths in a range from about 2 microns to about 10 microns.

Figure 2:
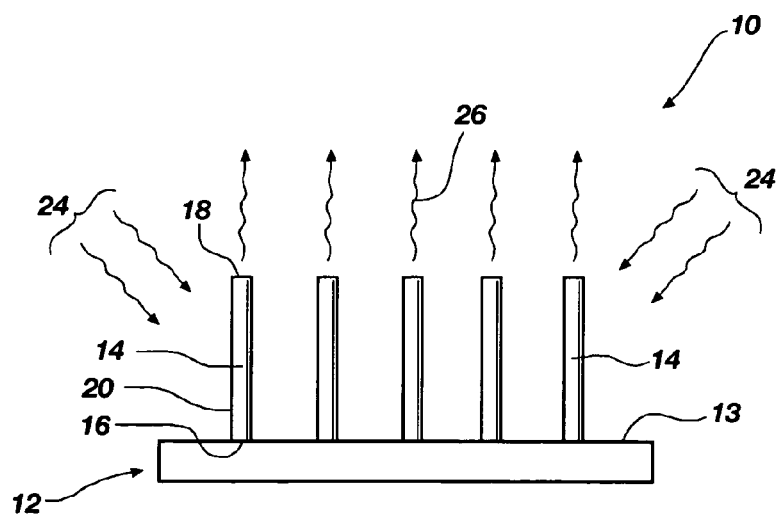
FIG. 2 is a side view of the representative nanostructure shown in FIG. 1 illustrating pump radiation and lased radiation.

Referring to FIG. 2, each ZnO nanoparticle 14 may grow as a single crystal along the <0001> direction and may be well-faceted at the bottom surface 16, the top surface 18, and the side surfaces 20 of the nanoparticle 14. Each ZnO nanoparticle 14 may behave as a natural laser cavity. The bottom surface 16 and the top surface 18 of each nanoparticle 14 may behave as mirrors in conventional laser cavities. In this configuration, each nanoparticle 14 of the nanostructure 10 is configured to emit lased radiation upon stimulation of the nanoparticle 14. The nanoparticles 14 may be stimulated by irradiating the nanoparticles 14 with pump radiation 24. For example, the nanoparticles 14 may be pumped with pump radiation at 266 nanometers using an yttrium-aluminum-garnet laser (3 nanosecond pulse width) at room temperature. The power of the pump radiation 24 may be greater than about 40 kilowatts per square centimeter. As illustrated in FIG. 2, each nanoparticle 14 may emit lased radiation 26 from the top surface 18 thereof upon such stimulation. For example, when the nanoparticles 14 are stimulated with pump radiation 24 having a wavelength of about 266 nanometers, the lased radiation 26 may have a wavelength of about 380 nanometers.

Figure 3:
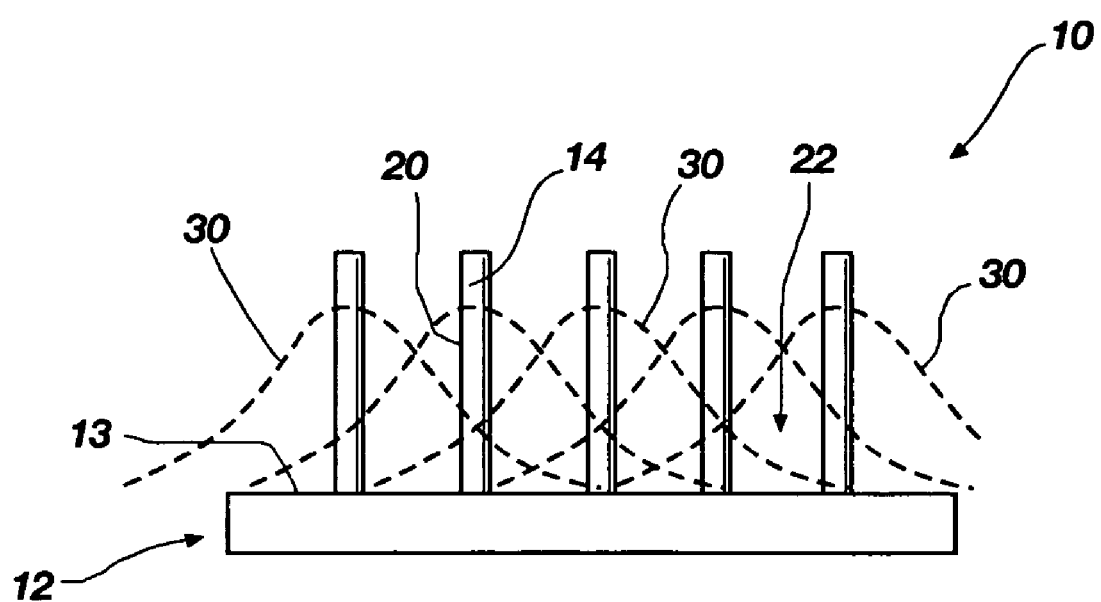
FIG. 3 is a side view of the representative nanostructure shown in FIG. 1 illustrating evanescent fields.

Referring to FIG. 3, an attenuating evanescent field may be generated by each nanoparticle 14 in the regions 22 laterally adjacent to the nanoparticle 14 when the nanoparticle is stimulated by, for example, pump radiation 24. The intensity of the attenuating evanescent field emitted from each nanoparticle 14 may decay exponentially from a maximum adjacent the lateral surface 20 thereof in a direction normal to the lateral surface 20. The exponentially decaying intensity of the attenuating evanescent field generated by each nanoparticle 14 of the nanostructure 10 is approximately represented in FIG. 3 by dashed lines 30. If the density of the nanoparticles 14 on the surface 13 of the substantially planar substrate 12 is sufficiently high, the evanescent fields generated by each nanoparticle 14 may couple to one another, resulting in relatively high optical power in the regions laterally adjacent the nanoparticles 14.

Figure 4:
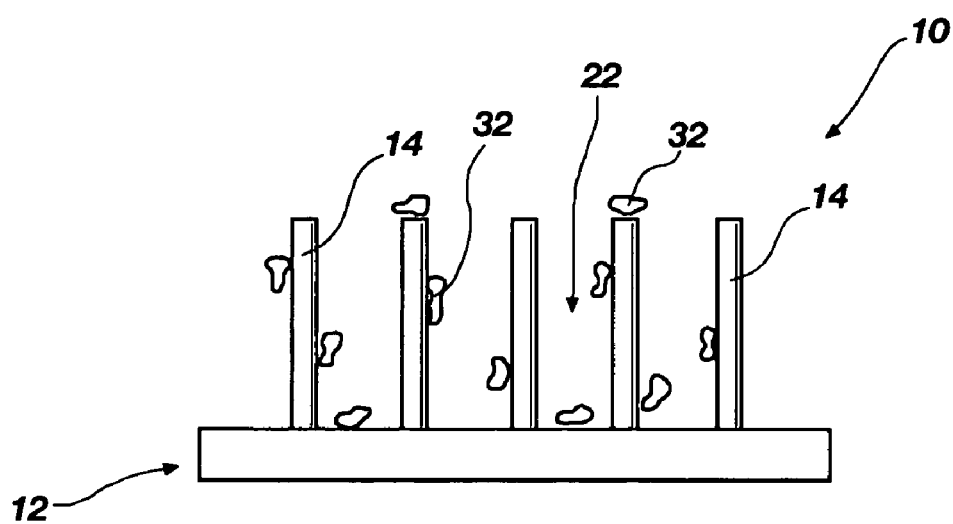
FIG. 4 is a side view of the representative nanostructure shown in FIG. 1 illustrating an analyte disposed on the nanostructure.

Referring to FIG. 4, an analyte 32 or a plurality of analytes 32 may be provided proximate the nanoparticles 14 of the nanostructure 10. The analyte 32 may be, for example, a biological molecule such as a protein. Each nanoparticle 14 may be stimulated by, for example, irradiating the nanoparticle 14 with pump radiation 24 (FIG. 2) as previously described. Stimulating the nanoparticles 14 may generate an evanescent field in the regions 22 laterally adjacent the nanoparticles 14, which may result in relatively high optical power in these regions 22. The Raman scattered radiation (not shown) scattered by the analyte 32 may be detected and analyzed to identify or study the analyte 32. In this manner, the nanostructure 10 may be used to perform Raman spectroscopy on the analyte 32.

As previously described, high optical power is required to conduct Raman spectroscopy because Raman scattering is a relatively weak process. By providing an analyte 32 in the regions 22 between the nanoparticles 14, the intensity of the Raman scattered radiation scattered by the analyte 32 may be enhanced. In this manner, the nanostructure 10 is configured to enhance the intensity of Raman scattered radiation scattered by an analyte 32.

In alternative embodiments of the present invention, the nanoparticles may comprise materials other than ZnO such as, for example, ZnS, CdS, GaN, and InP. Any nanoparticles that are configured to emit lased radiation upon stimulation of the nanoparticles may be used. For example, the nanoparticles 14 may comprise quantum dots that are configured to emit lased radiation upon stimulation. Certain photonic crystal structures are known to emit lased radiation. Densely packed photonic crystal lasers may be used to generate high optical power and may be used to provide nanostructures that embody teachings of the present invention.

Furthermore, the substantially planar substrate may comprise materials other than sapphire, such as, for example, Si, SiO, Ge, and ZnO. If the nanoparticles 14 are grown or synthesized on the substantially planar substrate 12, the material of the substrate may be selected to correspond to the material of the nanoparticle based on the match or mismatch between the lattice structure of the nanoparticles 14 and the lattice structure of the substantially planar substrate 12.

The nanoparticles 14 of the nanostructure 10 need not be grown or synthesized directly on the surface 13 of the substantially planar substrate 12. For example, a plurality of nanowire lasers may be grown or synthesized and then provided in a random orientation on the surface 13 of the substantially planar substrate 12. It is noted however, that the optical power provided by evanescent fields may be maximized by orienting the nanowire lasers 14 in a direction substantially parallel to one another.

Each nanoparticle 14 also may comprise a dopant, such as, for example, an ion of one of Mn, Cu, Ag, and Cr. By including a dopant in each nanoparticle 14, the wavelength of the lased radiation 26 and the evanescent fields emitted by each nanoparticle 14 may be varied. The variance in the wavelength may be at least partially a function of both the particular dopant selected and the concentration of the dopant in the nanoparticles 14.

Figure 5:
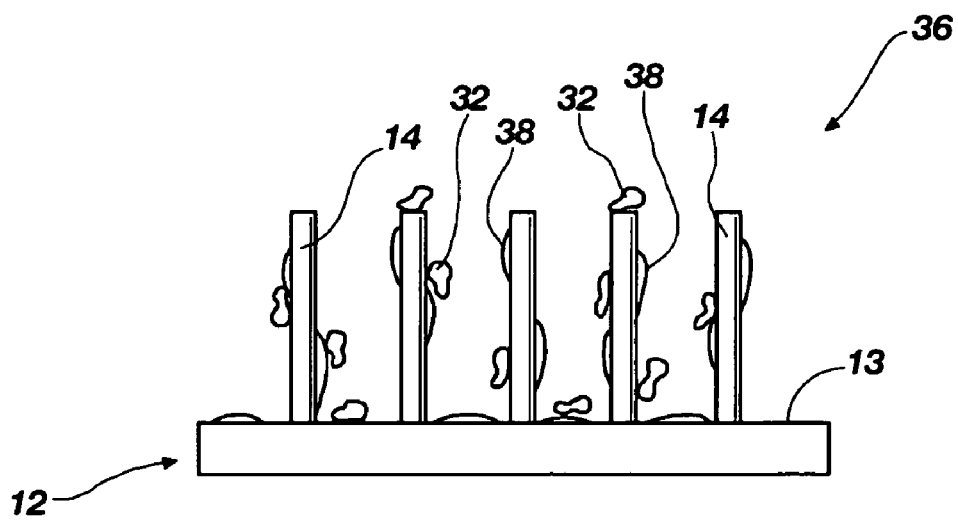
FIG. 5 is a side view of another representative nanostructure that embodies teachings of the present invention.

Another representative nanostructure 36 that embodies teachings of the present invention is shown in FIG. 5. The nanostructure 36 may be substantially similar to the nanostructure 10 shown in FIG. 1. In particular, the nanostructure 36 may include a substantially planar substrate 12 and a plurality of nanoparticles 14. The nanoparticles 14 are disposed on a surface 13 of the substantially planar substrate 12. Each nanoparticle 14 is configured to emit lased radiation 26 (FIG. 2) upon stimulation of the nanoparticle 14. The nanoparticles 14 may comprise nanowire lasers that extend from the surface 13 of the substantially planar substrate 12.

The nanostructure 36 further includes a Raman-enhancing material 38 disposed on a portion of each nanoparticle 14. Each nanoparticle 14 may be at least partially coated with the Raman-enhancing material 38. The Raman-enhancing material may comprise, for example, silver. Furthermore, the Raman-enhancing material may be configured as nanoparticles of Raman-enhancing material, which may be disposed on or among the nanoparticles 14 that are configured to emit lased radiation. For example, nanospheres of silver may be disposed on and among the nanoparticles 14. In this configuration, the Raman-enhancing material 38 may further enhance the intensity of the Raman scattered radiation that is scattered by an analyte 32.

Figure 6:
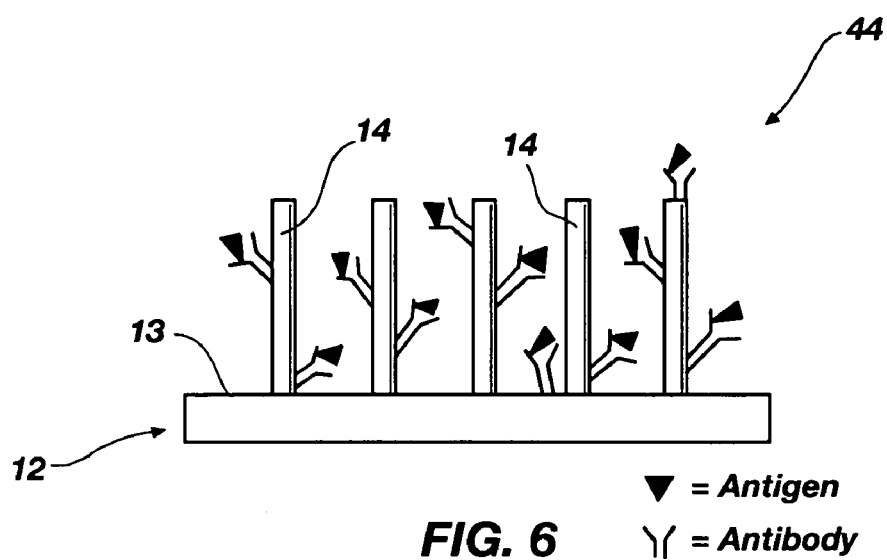
FIG. 6 is a side view of yet another representative nanostructure that embodies teachings of the present invention.

Another representative nanostructure 44 that embodies teachings of the present invention is shown in FIG. 6. The nanostructure 44 may be substantially similar to the nanostructure 10 shown in FIG. 1 and may include a substantially planar substrate 12 and a plurality of nanoparticles 14. The nanoparticles 14 are disposed on a surface 13 of the substantially planar substrate 12, and each nanoparticle 14 is configured to emit lased radiation 26 (FIG. 2) upon stimulation of the nanoparticle 14. The nanoparticles 14 may comprise nanowire lasers that extend from the surface 13 of the substantially planar substrate 12.

At least a portion of the surface of the nanoparticles 14 may be functionalized or derivatized to promote adherence of an analyte to the nanoparticles 14. In other words, the nanostructure 44 may further include a substance that is disposed on a surface of the nanoparticles 14 and configured to attract the analyte. For example, if the analyte is an antigen or an antibody, a complementary antigen or antibody may be provided on or adhered to the nanoparticles 14. As seen in FIG. 6, an antibody 46 may be adhered to the nanoparticles 14. If the complementary antigen 48 analyte is then provided proximate the antibody 46, the antibody 46 may bind to the antigen 48. Raman spectroscopy then may be conducted to identify and characterize the antigen 48 analyte as discussed previously. Many other methods for functionalizing or derivatizing surfaces to promote adherence of a particular analyte have been extensively researched and developed in the art of biosensors and bioassays and may be used to provide nanostructures that embody teachings of the present invention. These methods include, for example, attachment of receptors or ligands that promote the binding of a particular analyte. The ligand may be repulsive or neutral relative to molecules other than the analyte. The ligand and the analyte may consist of what is often referred to as a specific pair or a recognition pair of molecules.

Figure 7:
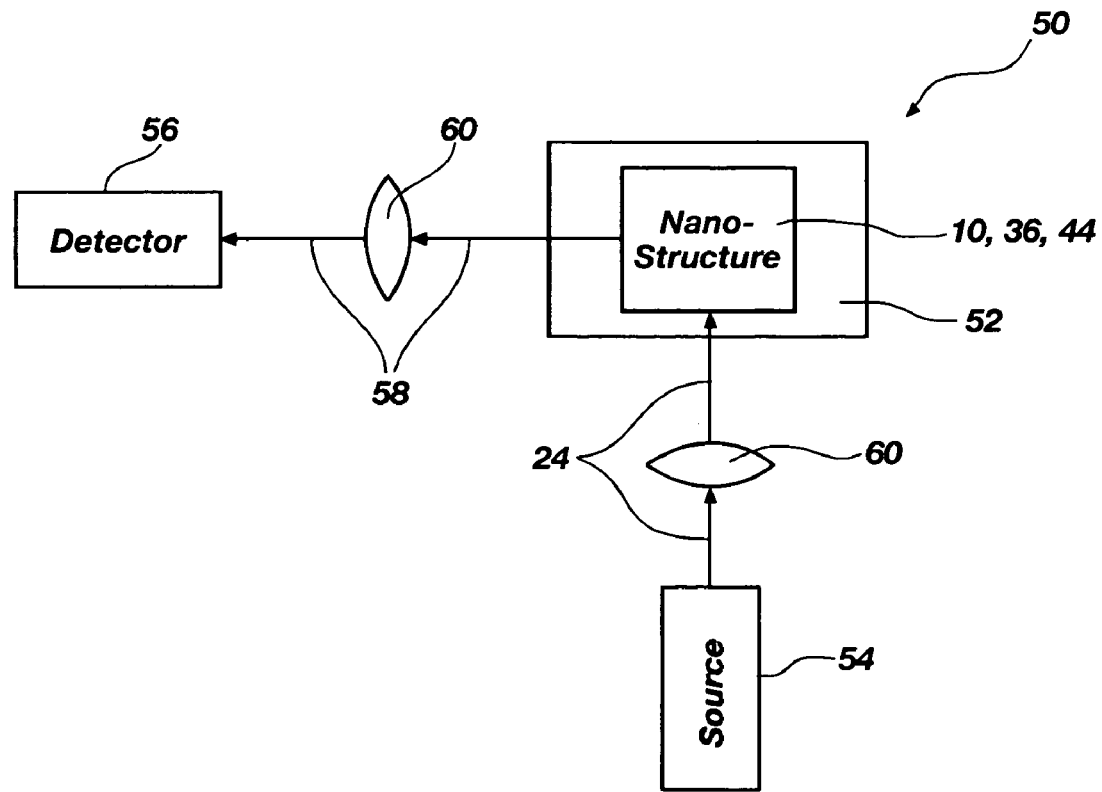
FIG. 7 is a schematic diagram of a representative Raman spectroscopy system that embodies teachings of the present invention.

Nanostructures that embody teachings of the present invention (for example, the nanostructure 10 shown in FIG. 1, the nanostructure 36 shown in FIG. 5, and the nanostructure 44 shown in FIG. 6) may be employed in Raman spectroscopy systems and used to perform Raman spectroscopy. A schematic diagram of a Raman spectroscopy system 50 that embodies teachings of the present invention is shown in FIG. 7. The Raman spectroscopy system 50 may include any one of the previously described nanostructures 10, 36, and 44. The Raman spectroscopy system 50 also includes means for stimulating the nanoparticles 14 (FIGS. 1-6) of the nanostructures 10, 36, and 44 and a detector 56 for detecting Raman scattered radiation 58. For example, the means for stimulating the nanoparticles 14 may include a radiation source 54 configured to emit pump radiation 24.

The Raman spectroscopy system 50 also may include an analyte stage 52 for holding or supporting the nanostructure 10, 36, 44 and the analyte (not shown). Furthermore, the Raman spectroscopy system 50 may include various optical components 60, such as, for example, lenses and filters, positioned between the radiation source 54 and the analyte stage 52, and positioned between the analyte stage 52 and the detector 56.

The radiation source 54 may include any suitable source for emitting pump radiation 24 at a desired wavelength and may be capable of emitting a tunable wavelength of pump radiation 24. For example, commercially available semiconductor lasers, helium-neon lasers, carbon dioxide lasers, radiation-emitting diodes, incandescent lamps, and any other known radiation-emitting sources can be used as the radiation source 54 so long as the radiation source 54 emits pump radiation 24 at a wavelength that will stimulate the nanoparticles 14 (FIGS. 1-6) as previously discussed.

Alternative means for stimulating the nanoparticles 14 may be used in particular embodiments of the present invention. For example, some nanoparticles 14 may be configured to emit lased radiation upon electrical stimulation. Electrical stimulation of a nanoparticle may be applied by, for example, providing at least two electrodes on the nanoparticle 14 and applying a voltage between the two electrodes across at least a portion of the nanoparticle 14.

The detector 56 receives and detects the Raman scattered radiation 58, which comprises Raman scattered photons that are scattered by the analyte. The detector 56 may include a device for determining the wavelength of the Raman scattered radiation 58 (for example, a monochromator) and a device for determining the intensity of the Raman scattered radiation 58 (for example, a photomultiplier). Typically, the Raman scattered radiation 58 is scattered in all directions relative to the analyte stage 52. Thus, the position of the detector 56 relative to the analyte stage 52 may not be particularly important. However, the detector 56 may be positioned at, for example, an angle of 90° relative to the direction of the pump radiation 24 to minimize the intensity of any pump radiation 24 that impinges on the detector 56.

Optical components 60 positioned between the source 54 and the analyte stage 52 can be used to collimate, filter, or focus the pump radiation 24 before the pump radiation 24 impinges on the analyte stage 52 and the nanostructure 10, 36, 44. Optical components 60 positioned between the analyte stage 52 and the detector 56 can be used to collimate, filter, or focus the Raman scattered radiation 58. For example, a filter or a plurality of filters may be employed to prevent radiation at wavelengths corresponding to the pump radiation 24 from impinging on the detector 56, thus allowing only the Raman scattered radiation 58 to be received by the detector 56.

To perform Raman spectroscopy using the Raman spectroscopy system 50, an analyte may be provided adjacent the nanostructure 10, 36, 44 as previously described. The nanostructure may then be irradiated with pump radiation 24 provided by the source 54 to stimulate the nanoparticles 14 (FIGS. 1-6) to emit lased radiation and to provide evanescent fields. Raman scattered radiation 58 scattered by the analyte may be detected by the detector 56. The nanostructure 10, 36, 44 may enhance the intensity of the Raman scattered radiation 58 as discussed previously. The wavelengths and corresponding intensity of the Raman scattered radiation 58 may then be determined and used to identify or provide information about the analyte.

It should be understood that Raman spectroscopy systems that embody teachings of the present invention may be provided in many forms, such as, for example, conventional table top systems or small portable Raman spectroscopy systems. For example, a representative Raman spectroscopy system that embodies teachings of the present invention may include a probe comprising a nanostructure 10, 36, 44. Fiber optic cables or wires may be used to transport the pump radiation 24 from the source 54 to the probe and to deliver Raman scattered radiation 58 from the probe to the detector 56. The source 54 and the detector 56 may be provided in a single portable unit to provide a relatively small, portable Raman spectroscopy system.

The nanostructures and Raman spectroscopy systems disclosed herein allow for improved Raman spectroscopy techniques and may be employed to enhance the intensity of Raman scattered radiation scattered by an analyte. Furthermore, the nanostructures and Raman spectroscopy systems also may be used to perform hyper-Raman spectroscopy and to enhance the intensity of hyper-Raman scattered radiation.

The performance of molecular sensors, nanoscale electronics, optoelectronics, and other devices employing the Raman Effect may be improved by using nanostructures and Raman spectroscopy systems that embody teachings of the present invention.

Moreover, the nanostructures and systems described herein may be useful for enhancing fluorescent signals, phosphorescent signals, and other types of signals in addition to Raman signals.

It is understood that, while various specific embodiments of the substrate have been described, the substrate on which the nanoparticles are grown need not be substantially planar. In alternative embodiments of the present invention, the substrate could also include a various other design features, such as, for example, a trench where the nanoparticles are grown on the two side walls and from the bottom of the trench. In this particular embodiment, the trench can be a conduit for fluid or gas to be analyzed. Also, in the case of a trench where the nanowire lasers are grown from the side walls, from one side wall to the other side wall, the walls, if electrically isolated can form the electrodes for electrically pumping the nanowire lasers.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A nanostructure configured to enhance the intensity of Raman scattered radiation scattered by an analyte, the nanostructure comprising:
    a substantially planar substrate;
    a plurality of nanoparticles extending in a substantially perpendicular direction from a surface of the substantially planar substrate, each nanoparticle of the plurality of nanoparticles being configured to emit lased radiation from a top surface thereof upon stimulation of the nanoparticle; and
    a Raman-enhancing material disposed on at least a portion of at least one nanoparticle.

2. A nanostructure as recited in claim 1, wherein the plurality of nanoparticles comprises a plurality of nanowire lasers extending from the surface of the substantially planar substrate.

3. A nanostructure as recited in claim 2, wherein each nanowire laser of the plurality of nanowire lasers extends in a direction substantially parallel to the other nanowire lasers.

4. A nanostructure as recited in claim 2, wherein each nanowire laser of the plurality of nanowire lasers comprises one of ZnO, ZnS, CdS, GaN, and InP.

5. A nanostructure as recited in claim 4, wherein each nanowire laser of the plurality of nanowire lasers further comprises a dopant.

6. A nanostructure as recited in claim 5, wherein the dopant comprises an ion of one of Mn, Cu, Ag, and Cr.

7. A nanostructure as recited in claim 2, wherein each nanowire laser of the plurality of nanowire lasers is at least partially coated with the Raman-enhancing material.

8. A nanostructure as recited in claim 1, further comprising a substance configured to attract an analyte disposed on at least a portion of the surface of at least one nanoparticle.

9. A nanostructure as recited in claim 1, wherein the substrate comprises one of Si, SiO, Ge, ZnO, and sapphire.

10. A nanostructure as recited in claim 1, wherein the Raman-enhancing material comprises one of Au, Ag, and Cu.

11. A nanostructure as recited in claim 1, further comprising an analyte disposed proximate to at least one nanoparticle and the Raman-enhancing material.

12. A Raman spectroscopy system comprising:
    a nanostructure configured to enhance the intensity of Raman scattered radiation scattered by an analyte, the nanostructure comprising at least one nanoparticle configured to emit lased radiation upon stimulation of the at least one nanoparticle;
    means for stimulating the at least one nanoparticle; and
    a radiation detector configured to detect Raman scattered radiation scattered by the analyte.

13. A Raman spectroscopy system as recited in claim 12, wherein the nanoparticle comprises a nanowire laser.

14. A Raman spectroscopy system as recited in claim 13, wherein the nanowire laser comprises one of ZnO, ZnS, CdS, GaN, and InP.

15. A Raman spectroscopy system as recited in claim 13, wherein the nanowire laser is configured to provide an evanescent field upon stimulation of the nanowire laser.

16. A Raman spectroscopy system as recited in claim 12, wherein the means for stimulating the at least one nanoparticle comprise a radiation source configured to provide pump radiation.

17. A Raman spectroscopy system as recited in claim 12, further comprising a Raman-enhancing material disposed on at least a portion of the nanostructure configured to enhance the Raman signal of an analyte.

18. A method for performing Raman spectroscopy comprising:
    providing a nanostructure configured to enhance the Raman scattered radiation scattered by an analyte, the nanostructure comprising at least one nanoparticle configured to emit lased radiation upon stimulation of the at least one nanoparticle;
    providing an analyte at a position proximate to the at least one nanoparticle;
    stimulating the at least one nanoparticle; and
    detecting Raman scattered radiation scattered by the analyte.

19. A method for performing Raman spectroscopy as recited in claim 18, wherein stimulating the at least one nanoparticle comprises irradiating the at least one nanoparticle with pump radiation.

20. A method for performing Raman spectroscopy as recited in claim 18, further comprising providing an evanescent field in a region comprising the position of the analyte.

21. A method for performing Raman spectroscopy as recited in claim 18, further comprising providing a Raman-enhancing material on at least a portion of the at least one nanoparticle.

* * * * *